United States Patent [19]

Scheinbeim et al.

[11] Patent Number: 5,369,995
[45] Date of Patent: Dec. 6, 1994

[54] HUMIDITY SENSOR

[75] Inventors: Jerry I. Scheinbeim, Somerset; Brian A. Newman, Highland Park, both of N.J.

[73] Assignee: Rutgers, The State University of New Jersey, New Brunswick, N.J.

[21] Appl. No.: 50,814

[22] Filed: Apr. 21, 1993

[51] Int. Cl.$^5$ .................. G01N 19/10; G01N 33/18
[52] U.S. Cl. ................ 73/335.02; 73/335.14; 73/DIG. 4
[58] Field of Search .......... 73/335.02, 335.11, 335.14, 73/29.03, DIG. 4; 340/602; 436/39

[56] References Cited

U.S. PATENT DOCUMENTS

| | | | |
|---|---|---|---|
| 4,221,129 | 9/1980 | Sidebottom et al. | 73/335.02 X |
| 4,656,383 | 4/1987 | Albert | 310/321 |
| 4,696,796 | 9/1987 | Oka et al. | 422/88 |
| 4,793,182 | 12/1988 | Djorup | 73/335.02 |
| 4,818,961 | 4/1989 | Takahashi et al. | 333/194 |
| 4,942,364 | 7/1990 | Nishijima et al. | 73/335.05 X |

FOREIGN PATENT DOCUMENTS 0128387 11/1978 Japan.
1386502 3/1975 United Kingdom.

OTHER PUBLICATIONS

Newman et al, J. Mat. Sci. 25 (1990) 1779–1783.
Lee et al, J. Polym. Sci. B, 29 (1991) 279–286.
Takase et al, Macromolecules 24 (1991) 6644–6652.
Rezvani, Appl. Phys. Lett., 34 (1979) 828.
Newman et al, Office of Naval Research Contract, Technical Report No. 3 (1988).
Newman et al, Office of Naval Research Contract, Technical Report No. 17 (1991).
Mathur et al, Office of Naval Research Contract, Technical Report No. 4 (1984).
Linvill, NSF Grant, Technical Report No. 4834-3 (1978).

Primary Examiner—Robert J. Warden
Assistant Examiner—Robert Carpenter
Attorney, Agent, or Firm—Leroy G. Sinn

[57] ABSTRACT

A humidity sensor device which utilizes a humidity-sensitive piezoelectric polymer film as a transducer element. In a preferred embodiment a pair of excitation electrodes and a pair of pickup electrodes are provided on such a polymer film, a suitable excitation voltage is applied to the excitation electrodes and the resultant transverse piezoelectric effects are detected in the form of an electrical output voltage from the pickup electrodes. The electrical output signal is converted to the humidity value of the gaseous environment based on a prior calibration. Typically, an odd nylon such as nylon-11 or nylon-7 is used for the piezoelectric element and a rectangular, uniform and porous graphite films are deposited thereon as electrodes. The humidity sensor device of this invention can be used over a wide temperature range and can withstand repeated exposure to harsh temperature conditions over a long period of time.

22 Claims, 2 Drawing Sheets

HUMIDITY SENSOR

TECHNICAL FIELD

The present invention relates to a novel humidity sensor in which a moisture-sensitive piezoelectric polymer film is used as a sensor element. The sensor is capable of measuring the relative humidity in gaseous atmosphere within a wide range of temperatures. The humidity sensing device of this invention is convenient, sensitive to humidity and stable against heat. It has a short response time and is relatively stable against chemical agents.

BACKGROUND ART

Accurate determination of moisture content in gaseous environment such as air is useful in a wide variety of situations. Convenient devices capable of such determination will find widespread commercial applications.

Although piezoelectricity has been known for a long time, early studies were confined to naturally-occurring inorganic piezoelectric crystalline materials such as quartz and tourmaline, and studies on artificially manufactured piezoelectric materials such as certain organic polymers have been a very recent development. Especially, studies on the effect of moisture on the piezoelectric properties of piezoelectric organic polymers have occurred only very recently.

The present invention is a novel application of thermally and chemically stable moisture-sensitive piezoelectric materials as a moisture sensor for determining the relative humidity of gaseous environment. The invention is especially useful in high temperature applications such as in food processing technology where moisture sensing and control at elevated temperatures are important for the quality control of the food products.

SUMMARY OF THE INVENTION

Provided by this invention is a humidity sensor device which comprises a humidity-sensitive piezoelectric transducer system, a mechanical system which maintains the transducer under a suitable tension and an interfacing electrical system comprising an electrical driving system and an electrical pickup system. Said humidity-sensitive piezoelectric transducer system comprises a humidity-sensitive piezoelectric polymer film and two or more pairs of electrodes provided on said film. Said electrical driving system applies an alternating excitation voltage to a portion or portions of the transducer and the electrical pickup system detects changes which occur in the electro-mechanical properties of said polymer film and produces an electrical output. Based on results of separate calibration experiments, said electrical output is converted to the relative humidity of the gaseous environment under which the humidity sensor device is placed.

Also provided by this invention is a humidity-sensitive piezoelectric transducer system suitable for determining the relative humidity of gaseous environment which comprises a humidity-sensitive piezoelectric polymer film and two or more pairs of electrodes provided on said film.

Also provided by this invention is a method of determining the relative humidity of gaseous environment which comprises using a humidity sensor device as described above, whereby an alternating excitation voltage is applied to a portion or portions of the polymer film as described above and resultant changes which occur in the electro-mechanical properties of said polymer film are detected in the form of an electrical output signal and the latter is converted to the relative humidity value of the gaseous environment.

DETAILED DESCRIPTION OF THE INVENTION

Figure 1:
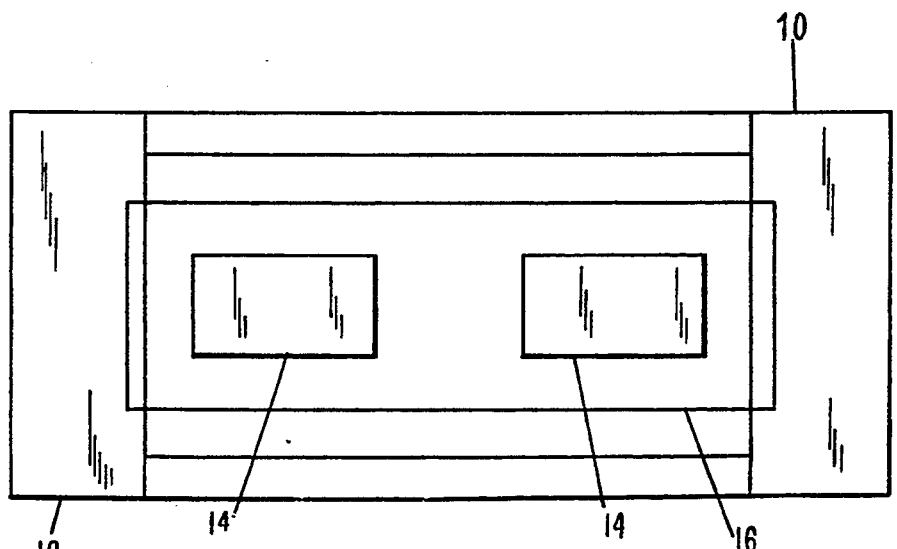
FIG. 1 a top view of a preferred embodiment of the humidity sensor device according to this invention depicting (a) its humidity-sensitive piezoelectric transducer system comprising a humidity-sensitive piezoelectric polymer film and two pairs of porous graphite electrodes, (b) a mechanical system which maintains said transducer system under a suitable tension, and (c) an interfacing electrical system comprising an electrical driving system and an electrical pickup system.

The piezoelectric polymer used in the humidity sensor device of this invention is an organic polymer having piezoelectric properties which are responsive to and substantially change with the relative humidity of the gaseous environment to which the polymer is exposed. Examples of such piezoelectric polymers suitable for this invention include so-called odd nylons which are polyamides of a straight-chain amino acid having an odd number of carbon atoms. Preferred examples of odd nylons suitable for this invention include nylon-11 and nylon-7. Nylon-11 is particularly preferred. Reasons for this include that films having high piezoelectric constants can be prepared by methods known to the art or preferably by a method described later in this specification, that the piezoelectric properties are stable over a wide temperature range, that substantial changes occur reversibly in the piezoelectric constants as a function of the relative humidity of the environment, that the material is relatively inert to various chemical agents, and hence that such films can be used for determining the relative humidity over a wide temperature range, namely, about 0° C. to 180° C. Preferred films used have superior mechanical properties as exhibited by high molecular weight polymers, such as toughness and impact and fracture resistance.

Other examples of humidity-sensitive piezoelectric polymers suitable for this invention include block copolymers between two or more odd nylons such as nylon-7/nylon-11 block copolymers.

Still other examples of humidity-sensitive piezoelectric polymers suitable for this invention include block copolymers between an odd nylon and another polymer and block copolymers between two or more odd nylons and another polymer.

Also included within the scope of the term "humidity-sensitive piezoelectric polymer" as used in the instant specification and the appended claims are compositions comprising a humidity-sensitive piezoelectric polymer such as those exemplified above and an additive material or materials such that the additive materials do not substantially affect the desired properties of the piezoelectric polymer. Thus, for instance, one can add suitable additives or dopants to the humidity-sensitive piezoelectric polymer of this invention according to each specific requirement or objective of application.

Nylon-11 can be synthesized by the polycondensation of 11-aminoundecanoic acid. Nylon-7 can be synthesized by the method described by Horn et al., J. Appl. Polym. Sci. 7 (1963) 887. Thus, a low molecular weight precursor polymer is obtained from ethyl 7-aminoheptanoate by polycondensation and thereafter the precursor is subjected to a second polycondensation step to afford a high molecular weight polyamide. Various methods known to the art can be utilized for preparing block copolymers comprising odd nylon units suitable for this invention.

Various methods known to the art can be used for preparing a humidity-sensitive piezoelectric film from a suitable polymeric material. Thus, in the case of nylon-11, as an example, one can use, for instance, the following procedure. The starting solid material is first pulverized into a fine powder and a thin film is prepared from a suitable amount of the powder with the aid of a hydraulic press. A well-crystallized film can be prepared by melting the material and pressing the film between aluminum foils with the aid of the hot press at a suitable temperature such as 210° C. The film may be allowed to cool slowly or quenched in an ice-water bath. The aluminum foils can be removed subsequently by a suitable chemical method, for instance, by use of an aqueous sodium hydroxide solution. The film may or may not be mechanically stretched. The stretching may be conducted, for instance, at room temperature at a suitable stretch ratio such as about 3:1. Typically, the film thickness is about 10–50 microns. Subsequently a thin aluminum foil is vapor-deposited on both sides of the polymer film to serve as electrodes for the "poling" procedure. The poling may be accomplished by applying a high electric field to the film in order to produce a permanent electric polarization in the film. The applied electric field may be, for instance, a triangular wave form having suitable period and maximum amplitude. The foregoing description, however, is presented by way of illustration only, and various other methods can also be used to prepare humidity-sensitive piezoelectric polymer films suitable for this invention.

It has been found that a process comprising five steps described below is particularly preferable for preparing humidity-sensitive piezoelectric polymer films suitable for the present invention. Thus, the process comprises, in this sequence, (a) melting a starting polymeric material to obtain a melted film, (b) quenching the melted film, (c) cold drawing the film, (d) polarizing the cold-drawn film by applying a suitable electric field thereto and (e) annealing the polarized film at a temperature lower than the crystalline melting temperature of the film. It has been found that this process affords a thermal stability of the electric polarization of the polymer film up to about the crystalline melting point of the material. For details of the process described above, the reader is referred to a commonly assigned copending U.S. patent application, Ser. No. 07/854,189, filed Mar. 20, 1992. Reasons why this process is particularly preferable for purposes of this invention include the fact that thermal stability of piezoelectric properties is highly desirable in order for the humidity sensor device of this invention to be useful over a wide temperature range and to maintain the original piezoelectric properties over a long period of usage which may entail repeated or prolonged exposure to harsh temperature conditions. It is believed that the annealing described above as step (e) serves to fix, stabilize and lock in the electric polarization accomplished in the preceding step (d).

Typically, it is convenient for purposes of this invention to prepare a rectangular shaped film, for instance, about 25 mm by 15 mm.

The moisture-sensitive piezoelectric polymer film may have either a mono-layer structure as illustrated above, or a multi-layer structure such as a bilaminate or trilaminate structure. In the case of a multi-layer structure, at least one of the layers must be a polymer having piezoelectric properties which are sufficiently responsive to changes in the relative humidity. It is much preferred that the remaining layer or layers be made of polymers having high piezoelectric constants. Although poly(vinylidene fluoride) by itself is not a preferred material as a single layer film, because it does not have a moisture sensitivity as good as that of nylon-11 or nylon-7, it can be used suitably in this invention as a component of a multi-layer film, because high piezoelectric constants can be accorded to poly(vinylidene fluoride) films by methods known to the art or by the preferred method described above. Thus, in the case of a bilaminate film, preferred examples include nylon 11/poly(vinylidene fluoride), nylon-7/poly (vinylidene fluoride) and nylon-11/nylon-7 films. One can prepare such moisture-sensitive, piezoelectric bilaminate films by various methods known to the art. Thus, for instance, one can co-melt separately prepared mono-layer films with the aid of a hot press and thereafter quench and cold draw the resultant bilaminate film and then polarize it by application of a suitable electric field. The resultant polarized film may be annealed. As mentioned earlier, the process comprising five steps described earlier is particularly useful for purposes of this invention whether the piezoelectric polymer film has a monolayer structure or a multilayer structure.

In a preferred embodiment of this invention, the humidity-sensitive transducer element has a simple structure, namely, a planar rectangular film which has two portions, namely, a driving portion (excitation portion) and a receiver portion (pickup portion). Typically the rectangular film has a dimension of about 25 mm by 15 mm. It is preferable to prepare two pairs of electrodes of identical size on both faces of said rectangular film. Typically, such electrodes are porous films which permit satisfactory passage of moisture therethrough. A gap is provided between the two adjacent ends of the electrodes. One pair of electrodes are used for driving the transducer and the other pair of electrodes are used for the pickup purposes. In order to permit satisfactory passage of moisture, it is preferable that a chemically-stable porous material be used for the electrodes. Thus, it is preferable to prepare the electrodes from fine particles of graphite. One can start out with a suitable liquid suspension of fine graphite particles and coat the liquid suspension over predetermined areas of the transducer film and thereafter dry the film in order to obtain a thin layer of porous graphite. It is convenient to use a mask over the transducer film in applying such a liquid suspension over the transducer film. It is preferable to have a small amount of a suitable adhesive agent in the liquid suspension so that the resultant porous graphite layer will adhere to the transducer film in a satisfactory manner. Typically, the size of each electrode is about 10 mm by 10 mm. A suitable conductive wire is connected to each electrode with the aid of a suitable material such as a conductive epoxy resin. The thickness of each electrode is suitably chosen based on consideration of various factors including the long-term stability and durability of the electrode and the rate of moisture passage (migration) through the electrode. The latter factor affects the response time of the moisture sensor. Typically, the thickness of each electrode is about 10 to 50 microns. The transducer structure described above is merely an example of preferred embodiments of this invention, and the present invention is not limited to the structure described above. One can conceive various other structures in order to obtain a desirable level of signal to noise ratio in the output of the transducer.

In the preferred embodiment described above, two opposite ends of the transducer film are clamped within a suitable frame made of a suitable material such as brass and a suitable mechanical tension is maintained in the film so as to keep the film flat. Excess mechanical tension is not desirable, because such tension may give rise to a creep phenomenon of the piezoelectric film.

Figure 1A:
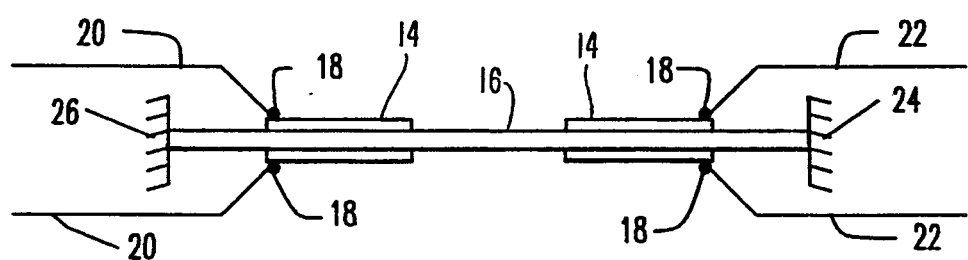
FIG. 1A is a side view of the humidity sensor device depicted in FIG. 1.

In one embodiment of the invention an excitation electrical voltage is applied to the excitation electrodes in order to induce a change in mechanical stress in the pickup portion of the transducer. The latter in turn produces an electrical output voltage in the pickup portion of the transducer. This pickup voltage can be detected and amplified by use of an electrical device known to the art. A typical set-up of various elements involved in this mode of operation of this invention is depicted in FIGS. 1 and 1A. FIG. 1 is a top view of the humidity sensor device and FIG. 1A is a side view thereof. The transducer depicted in FIGS. 1 and 1A can be characterized as a "push-pull" transducer.

In FIGS. 1 and 1A, items 10 and 12 represent end portions of a brass frame within which a piezoelectric nylon-11 film 16 is maintained under a certain tension (stress). The items 14 are porous graphite electrodes. One pair of electrodes 14 are used for the driving purposes and the other pair of electrodes 14 are used for the pickup purposes. Items 18 are connection means used to provide a suitable electrical connection between the porous graphite electrode 14 and a suitable conductive wire which is designated as item 20 where the wire is used for the driving portion of the transducer and as item 22 where the wire is used for the pickup portion of the transducer. Said item 18 is made of a conductive epoxy resin and items 20 and 22 are 30-gauge copper wires. Each of said connection means 18 is provided at a suitable location of the porous graphite electrode 14, for instance, at the midpoint of the edge portion facing item 10 or 12. A small gap is provided between the driving electrode 14 and the pickup electrode 14. Typically, the width of the gap is about 1 mm. Items 24 and 26 represent suitable mechanical devices used for applying a suitable mechanical tension to the opposite end portions of the nylon film 16.

Typically, the electrical voltage applied to the excitation portion of the transducer has a sinusoidal form with a peak value of $V_1$ and a frequency f. It is evident that as a general rule the output voltage $V_2$ becomes higher as the input voltage increases. Therefore, in order to obtain a sufficient signal-to-noise ratio in the output, it is preferable to apply a reasonably high input voltage $V_1$. However, one has to consider the fact that the electrical polarization originally present in the piezoelectric film may be depolarized if the input voltage becomes too high. Thus, one has to make a judicious choice of the input voltage based on these considerations. With regard to the frequency of the excitation voltage, it is generally preferable to use a low frequency, for instance, about 50–100 Hz in order to avoid errors which may be induced through cross coupling of the interfacing circuitry. As the excitation frequency is increased, capacitive coupling between the input and output becomes more difficult to control.

Theory suggests that the output voltage ($V_2$) of the pickup portion of the transducer is a function of the input voltage ($V_1$) applied to the excitation electrodes and the transverse electromechanical coupling coefficient ($k_{31}$) of the transducer film. The transverse electromechanical coupling coefficient $k_{31}$ in turn is a function of various parameters including the transverse piezoelectric charge coefficient ($d_{31}$), the permittivity and the Young's modulus of the material. Values of these physical properties of the material in turn vary depending upon temperature, relative humidity (moisture content) and the excitation frequency. Theory suggests that it is not necessary to know the individual values of these physical constants as a function of temperature, relative humidity and excitation frequency in order to determine the relative humidity of the gaseous environment under which the moisture-sensitive transducer is placed. Theory suggests that the ratio between the input voltage and the output voltage ($V_1/V_2$) is a function of the electromechanical coupling coefficient $k_{31}$ under given values of temperature, the moisture content of the transducer film and the frequency of excitation voltage. In the case of the transverse mode of operation described above as a preferred embodiment, the relation between $V_1/V_2$ and $k_{31}$ may be approximated as Equation 1 below. It has been found that in the case of a polarized nylon-11 film, for instance, the transverse electromechanical coupling coefficient (a dimensionless number) varies between about 0.01 and 0.025 for the relative humidity range of 40%–100% at 25° C.

$$(k_{31})^2 = \frac{2}{1 + V_1/V_2} \quad (1)$$

As mentioned earlier, the present invention is not limited to a transverse mode of operation. Instead, one can use a direct (thickness) mode of operation whereby an excitation voltage is applied across the transducer film and the resultant change in mechanical stress along the vertical direction is detected. The direct mode is particularly useful when one employs a multi-layered transducer film structure consisting of a plurality of piezoelectric film layers.

Before using the moisture sensor of this invention for actual measurements, it is necessary to carry out calibration experiments in order to determine the exact functional dependency between the relative humidity of the gaseous environment and the magnitude of the output signal which is typically the output voltage $V_2$ (which in turn is usually amplified). In order to carry out such calibration experiments, one uses a reference humidity sensor and places it side by side with the humidity sensor of this invention under the same gaseous environment. One can use various humidity sensors known to the art for this purpose. An example of such known reference humidity sensor is a capacitive-type humidity sensor which monitors the change in frequency of an oscillator controlled by the capacitive-type, humidity-sensitive element. One has to carry out such calibration experiments at each temperature. In this manner one obtains a functional relation between the output signal $V_2$ and the relative humidity at various values of temperature. Once this functional relation is obtained, one can utilize the humidity sensor of this invention for actual measurements by back-converting the output signal $V_2$ to the relative humidity of the environment. Of course, this conversion can be carried out electronically. Thus, one can obtain an on-line reading of the relative humidity of the gaseous environment in question. It has been found that the functional relation between the output voltage $V_2$ and the relative humidity is a well behaved monotonical function and therefore that the relative humidity can be determined with reasonable accuracy and precision.

Generally speaking, the response time varies depending upon various factors such as the thickness and physicochemical properties of the humidity-sensitive piezoelectric polymer film, thickness and porosity of the electrode present on the polymer film (assuming that porous electrodes are used; see further discussion below) and the size of the active area of the transducer film. It has been found that a response time of approximately a few minutes can be achieved according to the moisture sensor of this invention. Needless to said, the response time (speed) required or desired for the device varies depending upon each application. Thus, one should make a judicious choice of the electrode material, structure, shape and the like depending upon the response time required for each application.

In the preferred embodiment of this invention, the electrodes have a rectangular, uniform and porous film structure which permits migration of moisture therethrough. However, it is not essential that the electrodes have such a structure. Thus, the electrodes may have a more complicated shape than rectangular, such as a "finger shape," resembling a human hand. In such a case, the portions of the piezoelectric polymer film that are not covered with the electrode permit easier and faster migration of moisture therethrough than the portions of the polymer film that are covered with the electrode. In fact, in such a case, the electrode can be impervious to moisture. Thus, in such a case, one does not have to use a porous material for the electrode, but instead one can use, for instance, a thin film of a suitable metal such as gold. In the case of a "finger shaped" electrode, the functional relation between $V_1/V_2$ and the electromechanical coupling coefficient $k_{31}$ observed in the transverse mode of operation as described above will be different from the one observed for the situation where the electrodes have a rectangular, uniform and porous film structure, but still the general principles described above equally apply. Thus, one can conduct calibration experiments in order to determine the functional relationship between $V_1/V_2$ and the relative humidity, and based on this calibration one can back-convert each observed value of $V_1/V_2$ to the relative humidity.

Similarly, it is not essential that there be two and only two pairs of electrodes provided on the piezoelectric polymer film. Thus, for instance, one can provide four pairs of electrodes, namely, two pairs on the excitation portion of the polymer film and two pairs on the pickup portion of the polymer film. Again, the electrodes may not have a rectangular, homogeneous and porous film structure, but instead they may have a partially open structure such as a "finger shaped" structure.

It is an advantage of this invention that the relative humidity measurements can be conducted over a wide temperature range. Thus, in the case of a piezoelectric nylon-11 film, the measurements can be conducted over a temperature range of about 0 to 180° C. with a reasonable consistency without any substantial adverse effect on the transducer. It is another advantage of this invention that the transducer is chemically stable and can withstand relatively harsh conditions.

Since piezoelectric polymer films having a good thermal stability of piezoelectric properties can be manufactured with the aid of the aforementioned process comprising five steps, one can obtain, by using such a piezoelectric polymer film, a humidity sensor device according to this invention which can withstand repeated exposure to harsh temperature conditions.

As mentioned earlier in the "Summary of the Invention" section, the present invention also includes a humidity-sensitive piezoelectric transducer system suitable for determining the relative humidity of gaseous environments which system comprises a humidity-sensitive piezoelectric polymer film and two or more pairs of electrodes provided on the film. At least one pair of electrodes are used for the excitation purpose and at least one other pair of electrodes are used for the pickup purpose. The shape and structure of the electrodes must be such as to permit adequate migration of moisture either (a) from the gaseous environment, through the electrode and onto the polymer film or (b) directly from the gaseous environment to the polymer film. In the former case, the electrodes typically have a rectangular, uniform and porous film structure, whereas in the latter case, the electrodes typically have a partially open structure and they may be impervious to moisture.

Again as mentioned earlier, the present invention also includes a method of determining the relative humidity of a gaseous environment which comprises placing a humidity sensor device as described above under the gaseous environment, applying an alternating excitation voltage having suitable peak voltage and frequency to one or more pairs of excitation electrodes provided on the piezoelectric polymer film, while the film is maintained under a suitable tension, detecting the resultant electrical output signal from one or more pairs of pickup electrodes provided on the remaining portion or portions of the piezoelectric polymer film, and converting the latter to the relative humidity value of the gaseous environment based on a prior calibration.

The following example is presented in order to illustrate this invention. However, the invention is not limited to the example.

EXAMPLE 1

A push-pull type piezoelectric humidity sensor as depicted in FIGS. 1 and 1A was constructed.

(a) Sensor Element Fabrication

Nylon-11 granules obtained by polycondensation of 11-aminoundecanoic acid were first pressed at a temperature of 210° C. between aluminum foil sheets. The molten film was then quenched in an ice bath. Rectangular sections were cut from the resulting film and stretched by a ratio of 3:1 at room temperature. The resulting thickness of the film was about 30 microns.

Aluminum electrodes were vapor-deposited onto both sides of the film and the film was then poled. The poling process comprised subjecting the film to a high voltage triangular wave form with a period of 640s and a maximum amplitude of 150 MV/m. The poling field served to align the dipoles in the direction of the applied field.

The poled film was annealed by re-heating it to 185° C. (just below the melting point) followed by cooling. Annealing is used to stabilize the crystal structure of the nylon for use at high temperatures.

The aluminum electrodes were leached away in a 10% aqueous NaOH solution. Graphite electrodes were deposited onto both sides of the film using an air brush. The graphite was placed in the same locations as the aluminum to assure coverage of the active area of the film.

The "push-pull" transducer requires two piezoelectric areas on the same film. Since the entire film is piezoelectric, two active areas are produced. When processing the nylon film by hand, the entire film could not be poled because of the increased chance of film breakdown. The chance of a defect being present in the poled area is increased with the size of the area being poled. To over-come this problem only small areas of the nylon were poled at one time.

The film was masked during electrode deposition. This mask exposed two 24 mm$^2$ areas on each side of the film. The electrode pairs were each poled to create two piezoelectric areas on a single piece of film. After poling, the aluminum electrodes were replaced by porous graphite electrodes. The resulting film had two separate active areas placed approximately 2 mm apart.

(b) Transducer Construction and Interfacing Circuitry

The film was attached to either end of a rectangular opening in a brass frame (see FIG. 1). A constant tension was placed on the film in the same direction used to stretch the film during fabrication. A conductive epoxy resin was used to attach 30 gauge leads to the graphite electrodes. The leads were soldered to insulated conductive strips attached to the brass frame. Connection to the interfacing circuitry was made through these terminal strips. The brass frame was inserted into a brass tube and the tube attached to the enclosure that held the interfacing circuitry.

A BK Precision model 3020 sweep/function generator was connected to one of the active areas (driving element). The generator was configured to produce a 24 volt peak to peak sinusoidal wave at a suitable frequency for all tests. The other active area (pickup element) was connected to an instrumentation amplifier circuit shown in FIG. 2.

Figure 2:
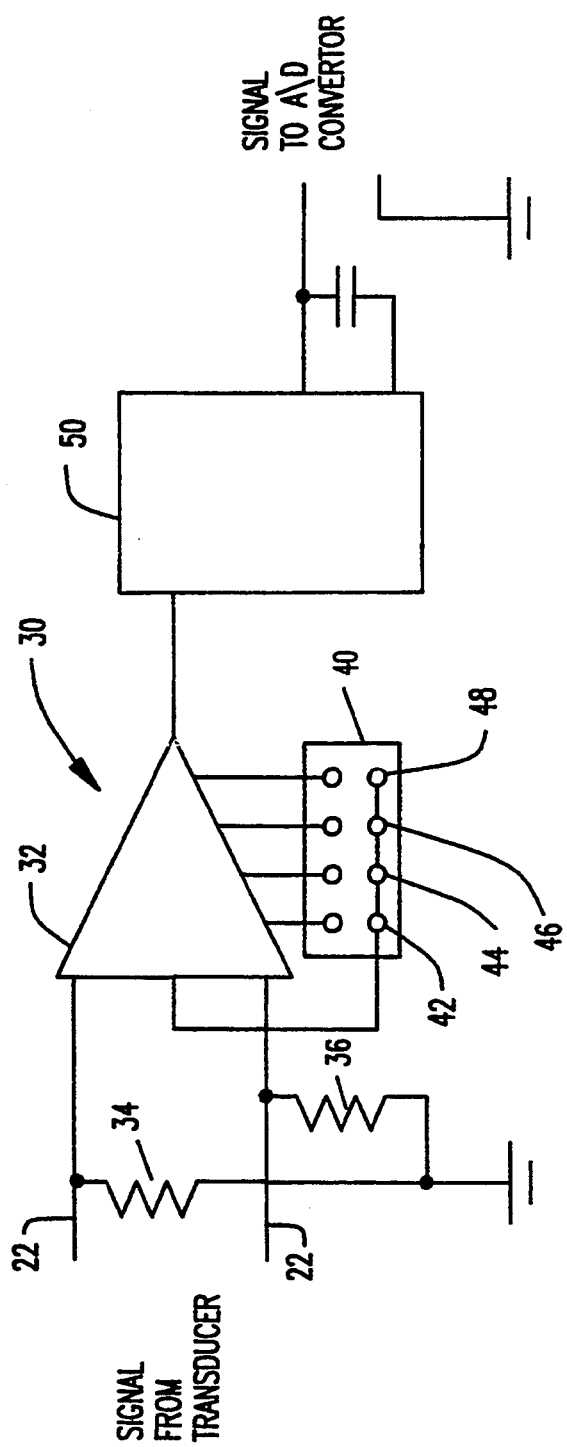
FIG. 2 is a diagram representing a signal conditioning circuit for the preferred humidity sensor device depicted in FIGS. 1 and 1A.

Referring to FIG. 2, the instrumentation amplifier 32 serves to isolate both electrodes of the pickup element from any stray capacitance that might couple the input signal to the output. Bias current required for the amplifier's input stages is produced by resistors 34 and 36. Items 22 represent continuations of the conductive wires shown in FIG. 1A also as items 22. The gain of this amplifier 32 is selected by using; a gain selector 40 comprising jumpers 42, 44, 46 and 48. Gain settings of 200 or 500 were used for most tests. The numeral 30 refers to the overall signal conditioning circuit depicted in FIG. 2.

The output of the instrumentation amplifier 32 is a voltage that is equivalent to the difference in voltage produced by the two inputs multiplied by the gain selected. The voltage is at the same frequency as the voltage applied to the driving element. The amplitude of this sinusoidal voltage is converted to a DC voltage by the RMS to DC converter integrated circuit 50. The DC output of 50 is fed to an analog to digital converter (not shown). The resulting digital value is representative of the amplitude of the sinusoidal voltage produced by the pickup element.

Digital values produced by the analog to digital converter are processed by a software program running on a personal computer. The analog voltage is converted into a digital word every 500 ms for all of the tests. The digital words are recorded onto the computer's floppy disk and used as an input to post processing programs. Temperature and humidity from a commercially available reference sensor are recorded simultaneously. The post processing produces graphical, tabular, and statistical representation of the data for analysis.

(c) Humidity Control

The reference and prototype sensors were placed in a sealed chamber approximately three inches apart. A short duct was used to transfer water vapor produced by an electronic humidifier into the chamber and also isolate the transducers from noise. The humidifier was manually controlled to provide 100% humidity measurements. After the humidity reached 100%, the humidifier was turned off and the chamber vented to return the humidity to ambient levels. The temperature was also monitored and found to be stable within $+/-2°$ C. throughout all measurement cycles.

The humidity reference used was manufactured by the Dranetz Corporation and utilizes a Vaisala capacitive type sensor. The interfacing circuitry of this sensor monitors the change in frequency of an oscillator controlled by the capacitive humidity element.

(d) Experimental Results

With the aid of the push-pull transducer the electromechanical coupling coefficient of the piezoelectric nylon-11 film is directly measured and the change of this coefficient with changing humidity and excitation frequency is recorded.

The electromechanical coupling coefficients $k_{31}$ was measured at 50 and 100 Hz. These measurements showed that the $k_{31}$ coefficient changed from 0.01 to 0.025 for humidity ranges of 40 to 100% at 25° C.

The response time of the push-pull transducer was found to be of the order of 2–3 minutes. Response time is dependent upon the film thickness, the electrode thickness and density, and the size of the active area of the film.

The graphite electrodes used on the prototype transducer were deposited by hand using an airbrush and a simple rectangular mask, Resistance measurements across the electrode indicated the approximate amount of coverage. Vapor deposition techniques using complex masks and controlled flow allow electrode geometry to be optimized for response time.

What is claimed is:

1. A humidity sensor device which comprises:
  a) a humidity-sensitive piezoelectric transducer system comprising a humidity-sensitive piezoelectric polymer film and at least two pairs of electrodes provided on the polymer film which permit passage of moisture from a gaseous environment surrounding the sensor device to the piezoelectric polymer film either via a partially open structure of the electrodes or through the electrodes due to a moisture permeable structure or property;
  b) a tension element for maintaining said film under a tension; and
  c) an electrical system which interfaces with said transducer comprising a driving element for applying an alternating excitation voltage to at least one of said at least two pairs of electrodes and a pickup element for detecting an electrical output voltage which arises in at least one pair of electrodes as a result of said excitation voltage, which sensor device being characterized in that (i) the piezoelectric properties of the transducer are sufficiently responsive to the moisture content of the gaseous environment under which it is placed such that an electrical output signal is obtained in the pickup element with application of an excitation input voltage to the transducer without substantially depolarizing it and that the electrical output is a monotonical function of said moisture content at any given temperature within a range of temperatures amenable to the humidity, measurement, said monotonical function enabling determination of the moisture content from the electrical output; and (ii) each of said electrodes permits adequate passage of moisture from the gaseous environment to the piezoelectric polymer film.

2. The humidity sensor device as defined in claim 1, wherein the piezoelectric polymer film consists essentially of an odd nylon.

3. The humidity sensor device as defined in claim 2, wherein the piezoelectric polymer film consists essentially of nylon-11.

4. The humidity sensor device as defined in claim 2, wherein the piezoelectric polymer film consists essentially of nylon 7.

5. The humidity sensor device as defined in claim 1, wherein the piezoelectric polymer film consists essentially of a block copolymer between odd nylons.

6. The humidity sensor device as defined in claim 1, wherein the electrodes are moisture-permeable.

7. The humidity sensor device as defined in claim 6, wherein the electrodes have a uniform porous structure adequate for permitting passage of moisture therethrough from the gaseous environment into the polymer film.

8. The humidity sensor device as defined in claim 7, wherein the electrodes are made of porous graphite.

9. The humidity sensor device as defined in claim 1, wherein the electrodes have a partially open structure.

10. The humidity sensor device as defined in claim 9, wherein the electrodes are made of a metallic film.

11. A humidity-sensitive piezoelectric transducer system suitable for determining the relative humidity of gaseous environments, which comprises:

a) a humidity-sensitive piezoelectric polymer film, and b) at least two pairs of electrodes provided on the polymer film which permit passage of moisture from a gaseous environment surrounding the transducer system to the piezoelectric polymer film either via a partially open structure of the electrodes or through the electrodes due to a moisture permeable structure or property; which transducer system being characterized in that (i) the piezoelectric properties of the transducer are sufficiently responsive to the moisture content of the gaseous environment under which it is placed such that an electrical output signal is obtained with application of an excitation input voltage to the transducer without substantially depolarizing it and that the electrical output is a monotonical function of said moisture content at any given temperature within a range of temperatures amenable to the humidity measurement, said monotonical function enabling determination of the moisture content from the electrical output; and (ii) each of said electrodes permits adequate passage of moisture from the gaseous environment to the piezoelectric polymer film.

12. The transducer system as defined in claim 11, wherein the piezoelectric polymer film consists essentially of an odd nylon.

13. The transducer system as defined in claim 12, wherein the piezoelectric polymer film consists essentially of nylon-11.

14. The transducer system as defined in claim 12, wherein the piezoelectric polymer film consists essentially of nylon-7.

15. The transducer system as defined in claim 11, wherein the piezoelectric polymer film consists essentially of a block copolymer between odd nylons.

16. The transducer system as defined in claim 11, wherein the electrodes are moisture-permeable.

17. The transducer system as defined in claim 16, wherein the electrodes have a uniform porous structure adequate for permitting passage of moisture therethrough from the gaseous environment into the polymer film.

18. The transducer system as defined in claim 17, wherein the electrodes are made of porous graphite.

19. The transducer system as defined in claim 11, wherein the electrodes have a partially open structure.

20. The transducer system as defined in claim 19, wherein the electrodes are made of a metallic film.

21. A method of determining the relative humidity of a gaseous environment which comprises placing a humidity sensor device as defined in claim 1 under the gaseous environment, applying an alternating excitation voltage to at least one pair of electrodes provided on the piezoelectric polymer film while the film is maintained under a tension, detecting the resultant electrical output signal from at least one pair of electrodes provided on the piezoelectric polymer film, and converting the output signal to the relative humidity value of the gaseous environment based on a prior calibration.

22. The method as defined in claim 21, wherein a humidity-sensitive piezoelectric film consisting essentially of an odd nylon is used for the transducer element.

* * * * *